United States Patent [19]
Banholzer et al.

[11] Patent Number: 5,610,163
[45] Date of Patent: Mar. 11, 1997

[54] ESTERS OF THIENYL CARBOXYLIC ACIDS AND AMINO ALCOHOLS AND THEIR QUATERNIZATION PRODUCTS

[75] Inventors: Rolf Banholzer, Ingelheim am Rheim; Rudolf Bauer, Wiesbaden; Richard Reichl, Ingelheim am Rheim, all of Germany

[73] Assignee: Boehringer Ingelheim GmbH, Ingelheim am Rhein, Germany

[21] Appl. No.: 405,111

[22] Filed: Mar. 16, 1995

Related U.S. Application Data

[63] Continuation of Ser. No. 254,324, Jun. 6, 1994, abandoned, which is a continuation of Ser. No. 100,822, Aug. 2, 1993, abandoned, which is a continuation of Ser. No. 838,724, Mar. 13, 1992, abandoned.

[30] Foreign Application Priority Data

Sep. 16, 1989 [DE] Germany ............ 39 31 041.8

[51] Int. Cl.$^6$ .................. A61K 31/435; C07D 401/00; C07D 451/12
[52] U.S. Cl. .................. 514/291; 514/304; 546/18; 546/91; 546/125
[58] Field of Search ............ 546/91, 125; 514/291, 514/304

[56] References Cited

U.S. PATENT DOCUMENTS 4,855,422  8/1989  Grimminster ............ 540/466

OTHER PUBLICATIONS

The Merck Index, 11th ed (1989), Merck and Co, Inc., pp. 242 and 802–803.

*Primary Examiner*—Philip I. Datlow
*Attorney, Agent, or Firm*—Robert P. Raymond; Alan R. Stempel; Mary-Ellen M. Devlin

[57] ABSTRACT

Compounds of the formula

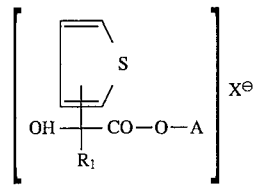

of which, in exemplary compounds, the thienyl group is attached via the 2-position and:
(a) A is 3α-(6β, 7β-epoxy)-tropanyl methobromide and $R_1$ is 2-thienyl;
(b) A is 3α-(6, 7dehydro)-tropanyl methobromide and $R_1$ is 2-thienyl;
(c) A is 3β-tropanyl methobromide and $R_1$ is 2-thienyl; and,
(d) A is 3α-(N-isopropyl)-nortropanyl methobromide and $R_1$ is cyclopentyl.

These are anticholinergics. Administered by inhalation, they are useful for the treatment of chronic obstructive bronchitis or slight to moderately severe asthma. Administered by the intravenous or oral routes, they are useful for the treatment of vagally induced sinus bradycardia.

16 Claims, No Drawings

ESTERS OF THIENYL CARBOXYLIC ACIDS AND AMINO ALCOHOLS AND THEIR QUATERNIZATION PRODUCTS

This is a continuation of application Ser. No. 08/254,324, filed on Jun. 6, 1994, now abandoned which is a continuation of application Ser. No. 08/100,822, filed on Aug. 2, 1993, now abandoned, which is a continuation of application Ser. No. 07/838,724, filed on Mar. 13, 1992, now abandoned.

The invention relates to novel thienylcarboxylates of amino alcohols and their quaternary products and to the preparation of the novel compounds and their use as active ingredients in medicaments.

The novel compounds correspond to the formula

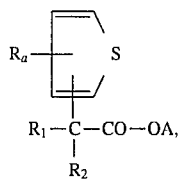

(I)

in which

A represents the group

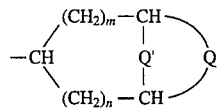

(II)

wherein m and n independently of one another denote 1 or 2,

Q represents one of the double-bonding groups

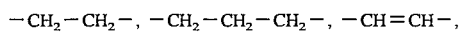

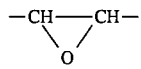

and

Q' represents the group =NR or the group =NRR', wherein

R denotes H or an optionally halogen-substituted or hydroxy-substituted $C_1$-$C_4$-alkyl radical, R' denotes a $C_1$-$C_4$-alkyl radical and R and R' together may also form a $C_4$-$C_6$-alkylene radical, and wherein, in the case of quaternary compounds, one equivalent of an anion (X⁻) opposes the positive charge of the N atom, $R_1$ represents a thienyl, phenyl, furyl, cyclopentyl or cyclohexyl radical, wherein these radicals may also be methyl-substituted, thienyl and phenyl may also be fluoro-substituted or chloro-substituted, $R_2$ represents hydrogen, OH, $C_1$-$C_4$-alkoxy or $C_1$-$C_4$-alkyl, $R_a$ represents H, F, Cl or $CH_3$ and, if =NR denotes a secondary or tertiary amino group, also the acid addition salts.

In the compounds of formula I, $R_1$ preferably represents thienyl, $R_2$ preferably represents OH. The group —OA preferably has the α-configuration and is derived from, for example scopine, tropine, granatoline or 6,7-dehydrotropine or the corresponding nor-compounds; however, —OA may also have the β-configuration, as in pseudotropine, pseudoscopine.

Corresponding radicals are, for example

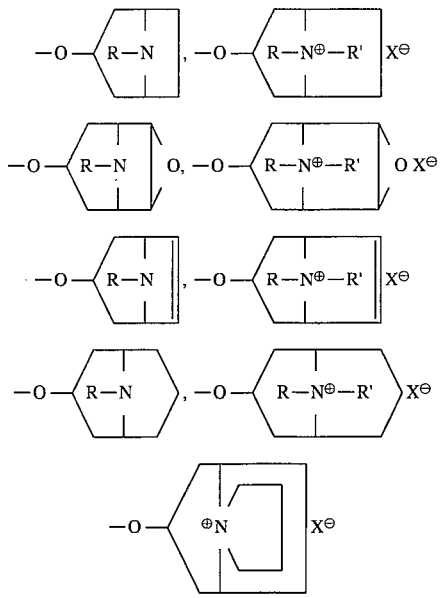

The substituent R is preferably a lower alkyl radical, such as $CH_3$, $C_2H_5$, n-$C_3H_7$, i-$C_3H_7$, R' is preferably $CH_3$. R and R' together are, for example —$(CH_2)_5$—. As halogen substituents for R, F or, as second choice, Cl are suitable.

If R denotes a halogen-substituted or hydroxy-substituted alkyl radical, it is preferably —$CH_2$—$CH_2F$ or —$CH_2$—$CH_2OH$. Accordingly, the group A represents, for example the radicals of scopine, N-ethylnorscopine, N-isopropylnorscopine, tropine, N-isopropylnortropine, 6,7-dehydrotropine, N-β-fluoroethylnortropine, N-isopropyl-6,7-dehydronortropine, N-methylgranatoline or the corresponding quaternary compounds, wherein the anion is preferably Br⁻ or $CH_3SO_3^-$.

As the acid radical

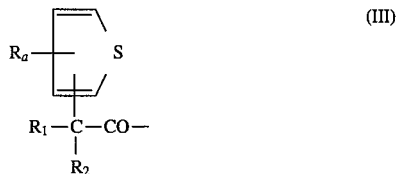

(III)

the following are particularly suitable:

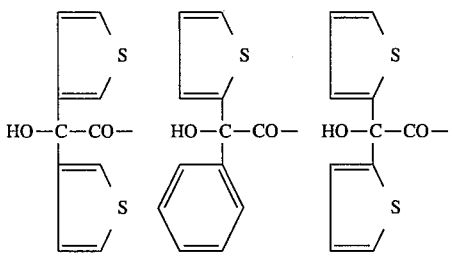

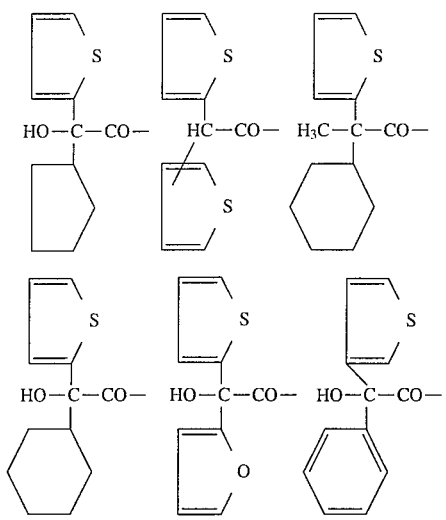

The quaternary compounds are particularly suitable for therapeutic application, whereas the tertiary compounds are important not only as active ingredients but also as intermediate products.

The compounds of the invention are strong anti-cholinergic agents and have prolonged action. Action lasting at least 24 hours is achieved at inhaled dosages in the µg range. In addition, the toxicity is in the same range as the commercial product Ipratropium bromide, while at the same time the therapeutic effect is stronger.

The novel compounds are suitable, in accordance with their anti-cholinergic nature, for example for the treatment of chronic obstructive bronchitis and (slight to moderately severe) asthma, also for the treatment of vagally induced sinus bradycardia.

Whereas application of the novel active ingredients (in particular the quaternary compounds) by inhalation is mainly recommended for respiratory tract diseases, as a result of which side-effects are largely eliminated, the application for sinus bradycardia is preferably carried out intravenously or orally. It has thus proved to be advantageous that the novel compounds leave the gastro/intestinal motility largely unaffected.

For administration the compounds of the invention are processed using known auxiliaries and/or excipients to give conventional galenic preparations, for example inhalation solutions, suspensions in liquified propellants, preparations containing liposomes or proliposomes, injection solutions, tablets, coated tablets, capsules, inhalation powders for use in conventional inhalation apparatus.

Formulation examples (measures in weight per cent):

| 1. Controlled dosage aerosol | |
|---|---|
| Active ingredient according to the invention | 0.005 |
| Sorbitan trioleate | 0.1 |
| monofluorotrichloromethane and Difluorodichloromethane 2:3 | to 100 |

The suspension is poured into a conventional aerosol container with a dosage valve. 50 µl of suspension are preferably dispensed per actuation. The active ingredient may also be metered in a higher amount if required (for example 0.02 wt. %).

| 2. Tablets | |
|---|---|
| Active ingredient according to the invention | 0.05 |
| Colloidal silicic acid | 0.95 |
| Lactose | 65.00 |
| Potato starch | 28.00 |
| Polyvinylpyrrolidone | 3.00 |
| Na cellulose glycolate | 2.00 |
| Magnesium stearate | 1.00 |

The constituents are processed in conventional manner to give tablets of 200 mg.

The advantageous properties of the novel compounds are shown, for example, in the inhibition of broncholysis in the rabbit (acetylcholine spasms intravenously). After intravenous administration of the novel active ingredients (dosage 3 µg/kg intravenously), the maximum effect occurred after 10 to 40 minutes. After 5 hours the inhibiting effect had still not been reduced to half, that is to say the half effect time is more, in some cases considerably more, than 5 hours, as made clear by the residual effects after 5 hours listed below:

| Compound | Residual effect in % |
|---|---|
| A | 76 |
| B | 76 |
| C | 81 |
| D | 61 |
| E | 68 |
| F | 73 |
| G | 69 |

-continued
Compounds of the formula
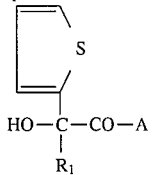
| Compound | A | $R_1$ |
|---|---|---|
| A | —O—[CH₃—N⁺—CH₃ ring] Br⁻, O | 2-thienyl |
| B | —O—[CH₃—N⁺—CH₃ ring] Br⁻, O | 3-thienyl |
| D | —O—[CH₃—N⁺—CH₃ ring] Br⁻ | 2-thienyl |
| E | —O—[CH₃—N⁺—CH₃ ring] Br⁻ | 3-thienyl |
| F | —O—[CH₃—N⁺—CH(CH₃)₂ ring] Br⁻ | cyclopentyl |
| G | —O—[CH₃—N⁺—CH₂—CH₂F ring] Br⁻ | cyclopentyl |
Compound C
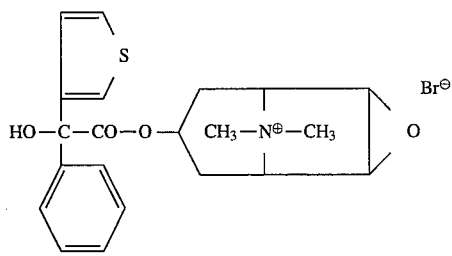
Notes:
1. The compounds in which $R_1$ is not 2-thienyl are racemates.
2. The compounds are 3α-compounds in each case.

Processes known per se are used to prepare the novel compounds.

An ester of the formula

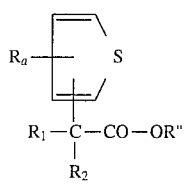 (IV)

wherein R" represents a $C_1$–$C_4$-alkyl radical, preferably a methyl or ethyl radical ($R_1$, $R_2$ and $R_a$ have the above meanings), is preferably transesterified using an amino alcohol of the formula

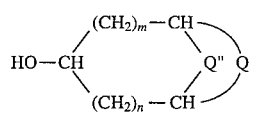 (V)

wherein m, n and Q have the above meanings, Q" represents =NR or =NH and the OH group is in the α- or β-position, in the presence of a conventional transesterification catalyst, and the compound obtained is optionally quaternised a) if Q" denotes =NR (R≠H), using a reactive monofunctionalised derivative Z-($C_1$–$C_4$-alkyl) of a corresponding alkane (Z=leaving group)

or is optionally quaternised b) if Q" denotes =NH, using a terminally disubstituted alkane Z-($C_4$–$C_6$-alkylene)-Z without isolation of intermediates.

The transesterification is carried out with heat in an organic solvent, for example toluene, xylene, heptane, or in a melt, strong bases such as sodium methylate, sodium ethylate, sodium hydride, metallic sodium, being used as catalyst. Reduced pressure is used to remove the released lower alcohol from the equilibrium, the alcohol is optionally distilled off azeotropically. The transesterification takes place at temperatures which in general do not exceed 95° C. Transesterification often proceeds more favourably in a melt. If required, the free bases may be obtained in a manner known per se from acid addition salts of the tertiary amines using suitable basic compounds. Quaternisation is carried out in suitable solvents, for example acetonitrile or acetonitrile/methylene chloride, preferably at room temperature; a corresponding alkyl halide, for example alkyl bromide, is preferably used in the process as quaternising agent. Transesterification products wherein Q' represents NH are used as starting materials for those compounds in which R and R' together represent a $C_4$–$C_6$-alkylene group. Conversion into the tertiary and then quaternary compound then takes place with the aid of suitable 1,4-dihaloalkanes, 1,5-dihaloalkanes or 1,6-dihaloalkanes without isolation of intermediates.

The starting materials may be obtained analogously to known compounds—in as much as they have not already been described.

EXAMPLES methyl di-(2-thienyl)glycolate from dimethyl oxalate and 2-thienyl magnesium bromide;

ethyl di-(2-thienyl)glycolate from (2-thienyl)glyoxylic acid and 2-thienyl lithium;

ethyl hydroxy-phenyl-(2-thienyl)acetate from methyl phenylglyoxylate and 2-thienyl magnesium bromide or from methyl (2-thienyl)glyoxylate and phenyl magnesium bromide.

Methyl 2-thienylglyoxylate and cyclohexyl or cyclopentyl magnesium bromide may be reacted in a similar manner.

Several processes are also available for the preparation of the amino alcohols.

Pseudoscopine may be obtained in accordance with M. Polonovski et al., Bull. soc. chim. 43, 79 (1928). Pseudotropenol may be removed from the mixture (fractional crystallisation or distillation) which is obtained, for example in accordance with V. Hayakawa et al., J. Amer. Chem. Soc. 1978, 100(6), 1786 or R. Noyori et al., J. Amer. Chem. Soc. 1974, 96(10), 3336.

The corresponding methyl esters may be prepared in a conventional manner starting from 2-furylglyoxylnitrile or 3-furylglyoxylnitrile via the 2-furylglyoxylic acid or 3-furylglyoxylic acid which can be obtained therefrom. The corresponding glycolates are obtained from these as described using the organometallic derivatives of 2-bromothiophene or 3-bromothiophene. The organometallic compounds which can be obtained from 2-, 3- or 4-halopyridine can be reacted with methyl 2-thienylglyoxylate or methyl 3-thienylglyoxylate to give the corresponding glycolates.

Thienylglycolates, in which the thiophene ring contains fluorine in the 2- or 3-position, are prepared, for example starting from 2-fluorothiophene or 3-fluorothiophene (bromination to give 2-bromo-3-fluorothiophene or 2-bromo-5-fluorothiophene), and after conversion to the corresponding organometallic compounds, reaction with suitable glyoxylates to give the glycolates.

2-Fluorothiophene and 3-fluorothiophene can be reacted analogously to give the corresponding glyoxylates Unterhalt, Arch. Pharm. 322, 839 (1989) which in turn, as already described, may be reacted with, for example 2-thienyl or 3-thienyl derivatives, to give glycolates. Symmetrically substituted di-thienylglycolates can be prepared analogously by selecting suitable components.

A further route is available via a process analogous to the benzoin condensation and benzilic acid rearrangement.

The following examples illustrate the invention without limiting it.

EXAMPLE 1

EXAMPLE 1

Scopine di-(2-thienyl)glycolate 50.87 g (0.2 mole) of methyl di-(2-thienyl)glycolate and 31.04 g (0.2 mole) of scopine are dissolved in 100 ml of absolute toluene and reacted at a bath temperature of 90° C. with addition of 1.65 g (0.071 gram atom) of sodium in several portions. The resulting methanol is distilled off at a reaction mixture temperature of 78°–90° C. under a pressure of 500 mbar. After a reaction time of about 5 hours, the reaction mixture is stirred into a mixture of ice and hydrochloric acid. The acid phase is separated off, rendered alkaline using sodium carbonate and the free base is extracted using methylene chloride. After drying over sodium sulphate, the methylene chloride is distilled off under reduced pressure and the residue is recrystallised from acetonitrile; beige-coloured crystals (from acetonitrile), m.p. 149°–50° C., Yield: 33.79 g (44.7% of theoretical).

EXAMPLE 2

Scopine di-(2-thienyl)glycolate 12.72 g (0.05 mole) of methyl di-(2-thienyl)glycolate and 7.76 g (0.05 mole) of scopine are melted in a heating bath at 70° C. under a water jet vacuum. 2.70 g (0.05 mole) of sodium methylate are introduced into this melt and heated for 1 hour in a heating bath at 70° C. under a water jet vacuum and subsequently for a further hour in a heating bath at 90° C. The solidified melt is taken up in a mixture of 100 ml of water and 100 ml of methylene chloride while monitoring the temperature, and the methylene chloride phase is extracted several times using water. The methylene chloride phase is extracted using the corresponding amount of dilute hydrochloric acid. The scopine di-(2-thienyl)glycolate is extracted from the combined aqueous phases using methylene chloride after adding the corresponding amount of sodium carbonate and dried over sodium sulphate. The hydrochloride is prepared from the dried methylene chloride solution in a conventional manner. The crystals are filtered off under suction, washed using acetone and dried under reduced pressure at 35° C. Pale yellow crystals (from methanol), m.p. 238°–41° C. (decomposition);

Yield: 10.99 g (53.1% of theoretical).

The hydrochloride may be converted to the base in a conventional manner.

EXAMPLE 3

Scopine di-(2-thienyl)glycolate 38.15 g (0.15 mole) of methyl di-(2-thienyl)glycolate and 23.28 g (0.15 mole) of scopine are mixed, 0.34 g (0.015 gram atom) of sodium is added and the mixture is melted in a heating bath at 90° C. under a water jet vacuum. The reaction lasts 2.5 hours. 100 ml of absolute toluene are then added and the mixture is stirred at a heating bath temperature of 90° C. until a solution is produced. The reaction solution is cooled to room temperature and stirred into a mixture of ice and hydrochloric acid cooled using ice. The hydrochloride of the basic ester crystallising out is filtered off under suction and washed using a small amount of water and a large amount of diethyl ether. The filtrate phases are separated off and the aqueous phase is extracted using diethyl ether. The hydrochloride filtered off under suction is suspended in the (acid) aqueous phase and converted to the base while monitoring the temperature and adding the corresponding amount of sodium carbonate; the base is extracted using methylene chloride. The combined methylene chloride phases are dried over sodium sulphate. After distilling off the methylene chloride, crystals remain which are purified over active charcoal and recrystallised from acetonitrile. Pale yellow crystals (from acetonitrile), m.p. 148°–49° C.;

Yield: 39.71 g (70.1% of theoretical).

TABLE I

Compounds of the formula

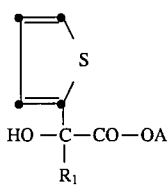

| No. | A | R₁ | Base | M.p. [°C.] Hydrochloride |
|---|---|---|---|---|
| 1 | 3α-(6β,7β-epoxy)-tropanyl | 2-thienyl | 149–50 | 238–41 |
| 2 | 3α-tropanyl | 2-thienyl | 167–8 | 253 |
| 3 | 3α-(6,7-dehydro)-tropanyl | 2-thienyl | 164–5 | |
| 4 | 3α-(N-β-fluoroethyl)-nortropanyl | 2-thienyl | | 236 |
| 5 | 3α-(N-isopropyl)-granatanyl | 2-thienyl | | 232 |
| 6 | 3α-(N-isopropyl)-nortropanyl | 2-thienyl | | 256 |
| 7 | 3α-(6β,7β-epoxy)-N-isopropyl-nortropanyl | 2-thienyl | | 206 |
| 8 | 3α-(6β,7β-epoxy)-N-ethyl-nortropanyl | 2-thienyl | | 212–3 |
| 9 | 3α-(N-ethyl)-nortropanyl | 2-thienyl | | 256–7 |
| 10 | 3α-(N-N-methyl)-granatanyl | 2-thienyl | | 241 |
| 11 | 3α-(6β,7β-epoxy)-N-β-fluoroethylnortropanyl | 2-thienyl | | 188–90 |
| 12 | 3α-(6β,7β-epoxy)-N-n-propylnortropanyl | 2-thienyl | | 104–6 |
| 13 | 3α-(6β,7β-epoxy)-N-n-butylnortropanyl | 2-thienyl | | 225–7 |
| 14 | 3α-(6β,7β-epoxy)-tropanyl | phenyl | | 246–7 |
| 15 | 3α-tropanyl | phenyl | | 243–4 |
| 16 | 3α-(N-β-fluoroethyl)-nortropanyl | phenyl | | 219–20 |
| 17 | 3α-(6,7-dehydro)-tropanyl | phenyl | | 181–3 |
| 18 | 3α-(N-ethyl)-nortropanyl | phenyl | | 231–2 |
| 19 | 3α-(N-isopropyl)-nortropanyl | phenyl | | 246–7 |
| 20 | 3α-tropanyl | cyclohexyl | | 260 |
| 21 | 3α-(N-β-fluoroethyl)-nortropanyl | cyclohexyl | | 203–4 |
| 22 | 3α-(6β,7β-epoxy)-tropanyl | cyclopentyl | | 237 |
| 23 | 3α-tropanyl | cyclopentyl | | 260 |
| 24 | 3α-(N-β-fluoroethyl)-nortropanyl | cyclopentyl | | 182–3 |
| 25 | 3α-(N-ethyl)-nortropanyl | cyclopentyl | | 227–8 |
| 26 | 3α-(N-isopropyl)-nortropanyl | cyclopentyl | | 174–5 |
| 27 | 3α-(6β,7β-epoxy)-tropanyl | 2-thienyl | | 240–2 |
| 28 | 3β-tropanyl | 2-thienyl | | 217–9 |
| 29 | 3β-(6,7-dehydro)-tropanyl | 2-thienyl | | 233–5 |
| 30 | 3α-(6,7-dehydro)-trapanyl | 3-thienyl | | 247–8 |
| 31 | 3α-(6β,7β-epoxy)-tropanyl | 3-thienyl | | 242–3 |
| 32 | 3α-(6β,7β-epoxy)-tropanyl | 2-furyl | | |
| 33 | 3α-(6,7-dehydro)-tropanyl | 2-furyl | | |
| 34 | 3α-tropanyl | 2-furyl | | |
| 35 | 3α-tropanyl | 2-pyridyl | | |
| 36 | 3α-(6β,7β-epoxy)-tropanyl | 2-pyridyl | | |
| 37 | 3α-(6,7-dehydro)-tropanyl | 2-pyridyl | | |
| 38 | 3α-tropanyl | 3-thienyl | | |
| 39 | 3α-(6,7-dehydro)-tropanyl | cyclopentyl | | |
| 40 | 3α-(6β,7β-epoxy)-tropanyl | cyclohexyl | | |
| 41 | 3α-(6,7-dehydro)-tropanyl | cyclohexyl | | |

Note: All hydrochlorides melt with decomposition.

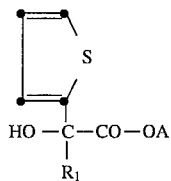

EXAMPLE 4

Scopine di-(2-thienyl)glycolate methobromide 10.0 g (0.0265 mole) of scopine di-(2-thienyl)glycolate are dissolved in a mixture comprising 20 ml of anhydrous methylene chloride and 30 ml of anhydrous acetonitrile and treated with 12.8 g (0.1325 mole) of methyl bromide (as 50% strength solution in anhydrous acetonitrile), and the reaction mixture is allowed to stand for 24 hours at room temperature in a tightly sealed reaction vessel. Crystals are precipitated during this time. They are filtered off under suction, washed using methylene chloride and dried at 35° C. under reduced pressure. White crystals (from methanol/acetone), m.p. 217°–8° C. (decomposition) after drying at 111° C. under reduced pressure.

TABLE II

Quaternary compounds of the formula

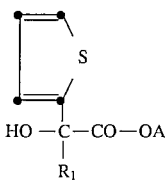

$$HO-\underset{R_1}{\overset{|}{C}}-CO-OA$$

| No. | A | $R_1$ | M.p. [°C.] |
|---|---|---|---|
| 1 | 3α-(6β,7β-epoxy)-tropanyl methobromide | 2-thienyl | 217–18 |
| 2 | 3α-tropanyl methobromide | 2-thienyl | 263–64 |
| 3 | 3α-(6,7-dehydro)-tropanyl methobromide | 2-thienyl | 191–92 |
| 4 | 3α-(N-β-fluoroethyl)-nortropanylmethobromide | 2-thienyl | 242–43 |
| 5 | 3α-tropanyl-β-fluoroethobromide | 2-thienyl | 214–15 |
| 6 | 3α-(N-isopropyl)-granatanyl methobromide | 2-thienyl | 229–30 |
| 7 | 3α-(N-isopropyl)-nortropanylmethobromide | 2-thienyl | 245–46 |
| 8 | 3α-(6β,7β-epoxy)-N-isopropyl-nortropanyl methobromide | 2-thienyl | 223–24 |
| 9 | 3α-(6β,7β-epoxy)-N-ethylnortrapanyl methobromide | 2-thienyl | 215–16 |
| 10 | 3α-(N-ethyl)-nortropanyl methobromide | 2-thienyl | 260–61 |
| 11 | 3α-(N-methyl)-granatanyl-methobromide | 2-thienyl | 246–47 |
| 12 | 3α-(6β,7β-epoxy)-N-fluoroethyl-nortropanyl methobromide | 2-thienyl | 182–83 |
| 13 | 3α-(6β,7β-epoxy)-N-n-propylnortropanyl methobromide | 2-thienyl | 209–10 |
| 14 | 3α-tropanyl-β-hydroxyethobromide | 2-thienyl | 231–32 |
| 15 | 3α-(6β,7β-epoxy)-tropanyl ethobromide | phenyl | 217–18 |
| 16 | 3α-tropanyl methobromide | phenyl | 273–74 |
| 17 | 3α-(N-β-fluoroethyl)-nortrapanylmethobromide | phenyl | |
| 18 | 3α-(6,7-dehydro)-tropanyl methobromide | phenyl | 110–71 |
| 19 | 3α-(N-ethyl)-nortropanyl methobromide | phenyl | 249–50 |
| 20 | 3α-(N-isopropyl)-nortropanyl methobromide | phenyl | 259–60 |

TABLE II-continued

Quaternary compounds of the formula

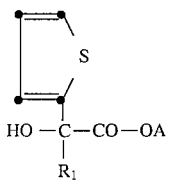

$$HO-\underset{R_1}{\overset{|}{C}}-CO-OA$$

| No. | A | $R_1$ | M.p. [°C.] |
|---|---|---|---|
| 21 | 3α-tropanyl ethobromide | phenyl | 248–49 |
| 22 | 3α-(N-ethyl)-nortropanyl ethobromide | phenyl | 244–45 |
| 23 | 3α-(6β,7β-epoxy)-tropanyl ethobromide | phenyl | 226 |
| 24 | 3α-tropanyl-β-fluoroethobromide | phenyl | 241 |
| 25 | 3α-tropanyl methobromide | cyclohexyl | 278 |
| 26 | 3α-(N-β-fluoroethyl)-nortropanyl methobromide | cyclohexyl | 198 |
| 27 | 3α-tropanyl-β-fluoroethobromide | cyclohexyl | 233–34 |
| 28 | 3α-tropanyl methobromide | cyclopentyl | 260 |
| 29 | 3α-tropanyl ethobromide | cyclopentyl | 235–36 |
| 30 | 3α-(N-ethyl)-nortropanyl methobromide | cyclopentyl | 251–52 |
| 31 | 3α-(N-isopropyl)-nortropanyl-methobromide | cyclopentyl | 244–45 |
| 32 | 3α-tropanyl-β-fluoroethobromide | cyclopentyl | 189–90 |
| 33 | 3α-(N-β-fluoroethyl)-nortropanyl-methobromide | cyclopentyl | 226–27 |
| 34 | 3α-(6,7-dehydro)-tropanyl metho-methanesulphonate | 2-thienyl | 225–6 |
| 35 | 3α-(6β,7β-epoxy)-tropanyl methobromide | 2-thienyl | 218–20 |
| 36 | 3α-tropanyl methobromide | 2-thienyl | 243–4 |
| 37 | 3α-(6,7-dehydro)-tropanyl methobromide | 2-thienyl | 211–4 |
| 38 | 3α-(6,7-dehydro)-tropanyl methobromide | 3-thienyl | 182–3* |
| 39 | 3α-(6β,7β-epoxy)-tropanyl methobromide | 3-thienyl | 217–8 |
| 40 | (+) enantiomer of No. 1 | | |
| 41 | (–) enantiomer of No. 1 | | |
| 42 | 3α-(6β,7β-epoxy)-tropanyl methobromide | 2-furyl | |
| 43 | 3α-(6,7-dehydro)-tropanyl methobromide | 2-furyl | |
| 44 | 3α-tropanyl methobromide | 2-furyl | |
| 45 | 3α-(6β,7β-epoxy)-tropanyl methobromide | 2-pyridyl | |
| 46 | 3α-(6,7-dehydro)-tropanyl methobromide | 2-pyridyl | |
| 47 | 3α-tropanyl methobromide | 2-pyridyl | |
| 48 | 3α-tropanyl methobromide | 3-thienyl | |
| 49 | 3α-(6,7-dehydro)-tropanyl methobromide | cyclopentyl | |
| 50 | 3α-(6β,7β-epoxy)-tropanyl methobromide | cyclohexyl | |
| 51 | 3α-(6,7-dehydro)-tropanyl methobromide | cyclohexyl | |
| 52 | 3α-(6β,7β-epoxy)-tropanyl methobromide | cyclopentyl | |

*contains crystalline methanol
Note: All compounds in the table melt with decomposition.

TABLE III

Compounds of the formula

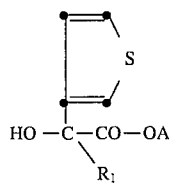

| No. | A | $R_1$ | M.p. [°C.] Hydrochloride |
|---|---|---|---|
| 1 | 3α-(6β,7β-epoxy)-tropanyl | phenyl | 246-7 |
| 2 | 3α-(6,7-dehydro)-tropanyl | phenyl | 261-2 |
| 3 | 3α-(6β,7β-epoxy)-tropanyl | 3-thienyl | |
| 4 | 3α-(6,7-dehydro)-tropanyl | 3-thienyl | |
| 5 | 3α-tropanyl | 3-thienyl | |
| 6 | 3α-(N-methyl)-granatanyl | 3-thienyl | |

TABLE IV

Compounds of the formula

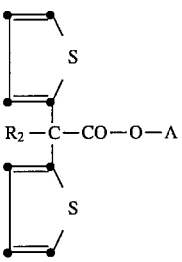

| No. | A | $R_2$ | M.p. [°C.] Hydrochloride |
|---|---|---|---|
| 1 | 3α-(6β,7β-epoxy)-tropanyl | H | |
| 2 | 3α-(6,7-dehydro)-tropanyl | H | |
| 3 | 3α-(6β,7β-epoxy)-tropanyl | methyl | |
| 4 | 3α-(6,7-dehydro)-tropanyl | methyl | 210-2.5 |
| 5 | 3α-(6β,7β-epoxy)-tropanyl | methoxy | |
| 6 | 3α-(6,7-dehydro)-tropanyl | methoxy | |

TABLE V

Compounds of the formula

| No. | A | $R_2$ | $R_a$ | M.p. [°C.] |
|---|---|---|---|---|
| 1 | 3α-(6β,7β-epoxy)-tropanyl | 2-thienyl | 5-methyl | |
| 2 | 3α-(6,7-dehydro)-tropanyl | 2-thienyl | 5-methyl | |
| 3 | 3α-tropanyl | 2-thienyl | 5-methyl | |
| 4 | 3α-(6β,7β-epoxy)-tropanyl | 2-(5-methyl)-thienyl | 5-methyl | |
| 5 | 3α-(6,7-dehydro)-tropanyl | 2-(5-methyl)-thienyl | 5-methyl | |
| 6 | 3α-tropanyl | 2-(5-methyl)-thienyl | 5-methyl | |
| 7 | 3α-(6β,7β-epoxy)-tropanyl | 2-thienyl | 5-fluoro | |
| 8 | 3α-(6,7-dehydro)-tropanyl | 2-thienyl | 5-fluoro | |
| 9 | 3α-tropanyl | 2-thienyl | 5-fluoro | |
| 10 | 3α-(6β,7β-epoxy)-tropanyl | 2-(5-fluoro)-thienyl | 5-fluoro | |
| 11 | 3α-(6,7-dehydro)-tropanyl | 2-(5-fluoro)-thienyl | 5-fluoro | |
| 12 | 3α-tropanyl | 2-(5-fluoro)-thienyl | 5-fluoro | |

TABLE VI

Compounds of the formula

| No. | A | $R_1$ | $R_a$ | M.p. [°C.] |
|---|---|---|---|---|
| 1 | 3α-(6β,7β-epoxy)-tropanyl methobromide | 2-thienyl | 5-methyl | |
| 2 | 3α-(6,7-dehydro)-tropanyl methobromide | 2-thienyl | 5-methyl | |
| 3 | 3α-tropanyl-methobromide | 2-thienyl | 5-methyl | |
| 4 | 3α-(6β,7β-epoxy)-tropanyl methobromide | 2-(5-methyl)-thienyl | 5-methyl | |

TABLE VI-continued

Compounds of the formula

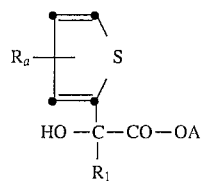

| No. | A | $R_1$ | $R_a$ | M.p. [°C.] |
|---|---|---|---|---|
| 5 | 3α-(6,7-dehydro)-tropanyl methobromide | 2-(5-methyl)-thienyl | 5-methyl | |
| 6 | 3α-tropanyl methobromide | 2-(5-methyl)-thienyl | 5-methyl | |
| 7 | 3α-(6β,7β-epoxy)-tropanyl methobromide | 2-thienyl | 5-fluoro | |
| 8 | α-(6,7-dehydro)-tropanyl methobromide | 2-thienyl | 5-fluoro | |
| 9 | 3α-tropanyl methobromide | 2-thienyl | 5-fluoro | |
| 10 | 3α-(6β,7β-epoxy)-tropanyl methobromide | 2-(5-fluoro)-thienyl | 5-fluoro | |
| 11 | 3α-(6,7-dehydro)-tropanyl methobromide | 2-(5-fluoro)-thienyl | 5-fluoro | |
| 12 | 3α-tropanyl methobromide | 2-(5-fluoro)-thienyl | 5-fluoro | |

TABLE VII

Compounds of the formula

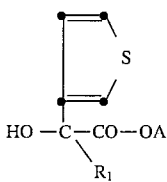

| No. | A | $R_1$ | M.p. [°C.] |
|---|---|---|---|
| 1 | 3α-(6β,7β-epoxy)-tropanyl methobromide | phenyl | 211–2 |
| 2 | 3α-(6,7-dehydro)-tropanyl methobromide | phenyl | 158–60* |
| 3 | 3α-(6β,7β-epoxy)-tropanyl methobromide | 3-thienyl | |
| 4 | 3α-(6,7-dehydro)-tropanyl methobromide | 3-thienyl | |
| 5 | 3α-tropanyl methobromide | 3-thienyl | |
| 6 | 3α-(N-methyl)-granatanyl methobromide | 3-thienyl | |

*(with crystalline methanol)

TABLE VIII

Quaternary compounds of the formula

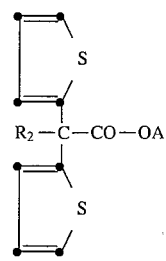

| No. | A | $R_2$ | M.p. [°C.] |
|---|---|---|---|
| 1 | 3α-(6β,7β-epoxy)-tropanyl methobromide | H | |
| 2 | 3α-(6,7-dehydro)-tropanyl methobromide | H | |
| 3 | 3α-(6β,7β-epoxy)-tropanyl methobromide | methyl | |
| 4 | 3α-(6,7-dehydro)-tropanyl methobromide | methyl | 206–8 |
| 5 | 3α-tropanyl methobromide | methoxy | |
| 6 | 3α-(N-methyl)-tropanyl methobromide | methoxy | |

We claim:

1. A compound of the formula

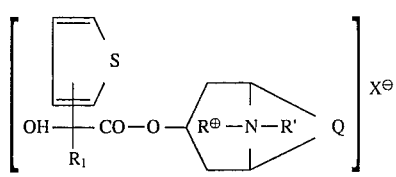

wherein

Q is a group of the formula —CH$_2$—CH$_2$—, —CH=CH— or

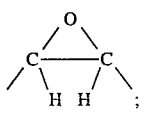

R and R' are each independently C$_1$–C$_4$-alkyl;

R$_1$ is thienyl, phenyl, cyclopentyl or cyclohexyl; and,

X$^-$ is a physiologically acceptable anion.

2. A compound in accordance with claim 1, of the formula

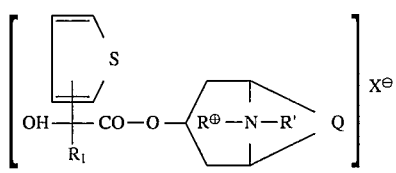

wherein

R is CH$_3$, C$_2$H$_5$, n-C$_3$H$_7$, or i-C$_3$H$_7$;

R' is CH$_3$; and,

R$_1$, Q and X$^-$ are as defined in claim 1.

3. A compound in accordance with claim 2 wherein R$_1$ is thienyl.

4. A compound in accordance with claim 2 wherein X$^-$ is Br$^-$ or CH$_3$SO$_3$.

5. A compound of the formula

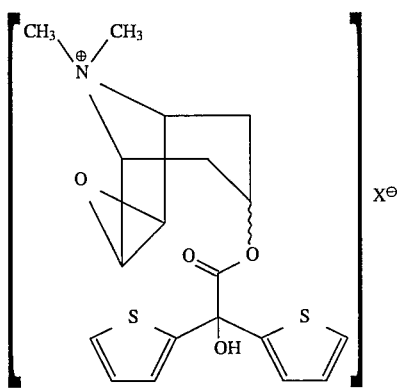

wherein X$^-$ is a physiologically acceptable anion.

6. A compound of the formula

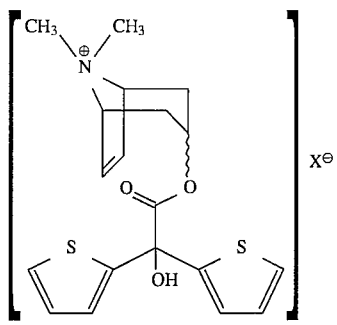

wherein X$^-$ is a physiologically acceptable onion.

7. A compound of the formula

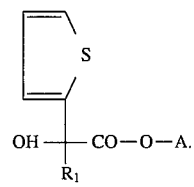

8. A compound of the formula

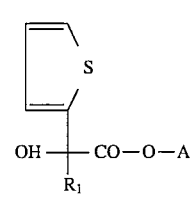

wherein R$_1$ is 2-thienyl and A is 3α-(6,7-dehydro)-tropanyl methobronide.

9. A compound of the formula

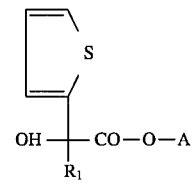

wherein R$_1$ is 2-thienyl and A is 3β-tropanyl methobromide.

10. A compound of the formula

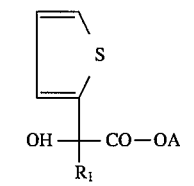

wherein R$_1$ is cyclopentyl and A is 3α-(N-isopropyl)-nortropanyl methobromide.

11. A method for treating chronic obstructive bronchitis which comprises administering, by inhalation, to a subject suffering from the same, a therapeutic amount of a compound in accordance with claims 1, 2, 3, 4 6, 7, 8, 9, 10.

12. A method for treating slight to moderately severe asthma which comprises administering, by inhalation, to a subject suffering from the same, a therapeutic amount of a compound in accordance with claims 1, 2, 3, 4, 6, 7, 8, 9, 10.

13. A method for treating vagally induced sinus bradycardia which comprises administering, by the intravenous or oral routes, to a subject suffering from the same, a therapeutic amount of a compound in accordance with claims 1, 2, 3, 4, 6, 7, 8, 9, 10.

14. A pharmaceutical composition, for administration by inhalation, suitable for the treatment of chronic obstructive bronchitis or slight to moderately severe asthma, which comprises a compound in accordance with claims 1, 2, 3, 4, 6, 7, 8, 9, 10.

15. A pharmaceutical composition, for oral administration, suitable for the treatment of vagally induced sinus bradycardia, which comprises a compound in accordance with claims 1, 2, 3, 4, 6, 7, 8, 9, 10.

16. A pharmaceutical composition, for intravenous administration, suitable for the treatment of vagally induced sinus bradycardia, which comprises a compound in accordance with claims 1, 2, 3, 4, 6, 7, 8, 9, 10.

* * * * *

UNITED STATES PATENT AND TRADEMARK OFFICE
CERTIFICATE OF CORRECTION

PATENT NO : 5,610,163
DATED : March 11, 1997
INVENTOR(S) : Rolf Banholzer, Rudolf Bauer and Richard Reichl It is certified that error appears in the above-identified patent and that said Letters Patent is hereby corrected as shown below:

In column 18, in the last line of Claim 6, change "onion" to --anion--.

Signed and Sealed this

Fourth Day of July, 2000

Attest:

Q. TODD DICKINSON

*Attesting Officer*     *Director of Patents and Trademarks*

UNITED STATES PATENT AND TRADEMARK OFFICE
CERTIFICATE OF CORRECTION

PATENT NO. : 5,610,163
DATED : March 11, 1997
INVENTOR(S) : Rolf Banholzer, Rudolf Bauer and Richard Reichl It is certified that error appears in the above-identified patent and that said Letters Patent is hereby corrected as shown below:

On the title page item [73], change "Boehringer Ingelheim GmbH" to
--Boehringer Ingelheim KG--.

Signed and Sealed this

Thirtieth Day of January, 2001

Attest:

Q. TODD DICKINSON

*Attesting Officer*    *Director of Patents and Trademarks*

UNITED STATES PATENT AND TRADEMARK OFFICE
CERTIFICATE OF CORRECTION

PATENT NO. : 5,610,163
DATED : March 11, 1997
INVENTOR(S) : Rolf Banholzer, Rudolf Bauer and Richard Reichl It is certified that error appears in the above-identified patent and that said Letters Patent is hereby corrected as shown below:

<u>Title page,</u>
Item [73], Assignee, change "Boehringer Ingelheim GmbH" to -- Boehringer Ingelheim KG --.

<u>Column 18,</u>
Line 25, (immediately following the structural formula and before claim 8), insert
-- wherein $R_1$ is 2-thienyl and A is 3α-(6β, 7β-epoxy)-tropanyl methobromide. --
Line 37, change "methobronide" to -- methobromide --.
Line 63, change "claims 1, 2, 3, 4, 6, 7, 8, 9 10" to -- claims 1, 2, 3, 4, 6, 7, 8, 9 or 10 --.

<u>Column 19,</u>
Line 4, change "claims 1, 2, 3, 4, 6, 7, 8, 9 10" to -- claims 1, 2, 3, 4, 6, 7, 8, 9 or 10 --.
Lines 8 to 9, change "claims 1, 2, 3, 4, 6, 7, 8, 9 10" to -- claims 1, 2, 3, 4, 6, 7, 8, 9 or 10 --.

<u>Column 20,</u>
Lines 1 to 2, change "claims 1, 2, 3, 4, 6, 7, 8, 9 10" to -- claims 1, 2, 3, 4, 6, 7, 8, 9 or 10 --.
Line 6, change "claims 1, 2, 3, 4, 6, 7, 8, 9 10" to -- claims 1, 2, 3, 4, 6, 7, 8, 9 or 10 --.
Line 10, change "claims 1, 2, 3, 4, 6, 7, 8, 9 10" to -- claims 1, 2, 3, 4, 6, 7, 8, 9 or 10 --.

Signed and Sealed this

Third Day of December, 2002

JAMES E. ROGAN
*Director of the United States Patent and Trademark Office*